(12) United States Patent
Futamura et al.

(10) Patent No.: US 6,569,845 B1
(45) Date of Patent: May 27, 2003

(54) NEOVASCULARIZATION INHIBITOR CONTAINING DIENOGEST AS THE ACTIVE INGREDIENT

(75) Inventors: Yoshihiro Futamura, Kanagawa (JP); Masaki Nakamura, Tokyo (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/582,428

(22) PCT Filed: Dec. 25, 1998

(86) PCT No.: PCT/JP98/05944

§ 371 (c)(1),
(2), (4) Date: Jun. 26, 2000

(87) PCT Pub. No.: WO99/33856

PCT Pub. Date: Jul. 8, 1999

(30) Foreign Application Priority Data

Dec. 26, 1997 (JP) .............................................. 9-369540

(51) Int. Cl.[7] .............................................. A61K 31/56
(52) U.S. Cl. ........................................ 514/178; 514/179
(58) Field of Search ................................. 514/179, 181

(56) References Cited

U.S. PATENT DOCUMENTS 5,652,231 A * 7/1997 Shibutani et al.
5,693,629 A   12/1997 Hibino et al.
6,242,481 B1 * 6/2001 Udagawa et al. ........... 514/468

FOREIGN PATENT DOCUMENTS

DE  43 21 957       * 12/1995
EP  0 654 267 A1    5/1995
WO  9526974         10/1995

OTHER PUBLICATIONS

Shubert et al., Natural Products Chemistry, 1984, Elsevier Science Publishers eds., 1985, pp. 143–158.
English Language Abstract of JP07188026A.
Katsuki et al., Cancer, 79, pp. 169–176 (1997).
Folkman et al., Science, 235, pp. 442–447 (1987).
Sugino et al., Chemical Pharmaceutical Bulletin, 45(2), pp. 421–423 (1997).
Yamamoto et al., International Journal of Cancer, 56, pp. 393–399 (1994).
Jikihara et al., American Journal of Obstetrics and Gynecology, 167(1), pp. 207–211 (1992).
Crum et al., Science, 230, pp. 1375–1378 (1985).
Hori et al., British Journal of Pharmacology, 118, pp. 1584–1591 (1996).
Hoffman et al., Exp. Clin. Endocrinol. (1983), 81(2), 146–157.*
Nakamura et al., European J. of Pharm., vol. 386, pp. 33–40, 1999.*

* cited by examiner

Primary Examiner—Barbara P. Badio
(74) Attorney, Agent, or Firm—Birch, Stewart, Kolasch & Birch, LLP

(57) ABSTRACT

A suppressing agent of angiogenesis that contains dienogest or a solvate thereof as the effective ingredient, and a prophylactic and/or therapeutic agent of angiogenic diseases, utilizing a novel action of dienogest.

5 Claims, 2 Drawing Sheets

NEOVASCULARIZATION INHIBITOR CONTAINING DIENOGEST AS THE ACTIVE INGREDIENT

This application is the national phase under 35 U.S.C. §371 of PCT International Application No. PCT/JP98/05944 which has an International filing date of Dec. 25, 1998, which designated the United States of America.

FIELD OF THE INVENTION

The present invention relates to a suppressing agent of angiogenesis, wherein the agent contains dienogest as the effective ingredient.

BACKGROUND OF THE INVENTION

Dienogest is the International Nonproprietary Name (INN) of a known compound with the following structure (17 α-cyanomethyl-17 β-hydroxy-estra-4, 9(10)-dien-3-one) represented by the following formula (1).

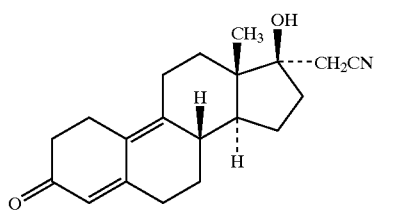

The properties of the compound and a method for synthesizing the compound are generally described by Shubert, et al., Natural Products Chemistry 1984, Elsevier Science Publishers eds., 1985, pp. 143–158.

Dienogest has been known to have progestational activity. In Germany, a combined drug of dienogest with ethinylestradiol has been introduced as an oral contraceptive into market. Additionally, the clinical development of dienogest as a therapeutic agent of endometriosis is ongoing (Kohler et al., Archives of Gynecology and Obstetrics, Vol. 254, pp. 594–595, 1993), and experimental reports have been issued to demonstrate the carcinostatic action of dienogest on uterine cancer and breast cancer (Katsuki et al., Japanese Patent Laid-open No. Hei 7-188026; Katsuki, et al., Cancer, Vol. 79, pp. 169–176, 1997). However, no report has been published yet to tell that dienogest has an action to suppress angiogenesis.

Angiogenesis is involved in normal physiological phases in humans and animals, such as embryo development and ovulation or placenta formation due to the female sex cycle and is also responsible for wound healing and the repair process of inflammation. Furthermore, it has been known that angiogenesis is also involved in many of pathologic conditions caused by rapid growth and proliferation of capillary vessel, leading to severe damage on tissues. The diseases caused by such pathologic increase of capillary vessel is called as so-called angiogenic diseases (Folkman et al., Science, Vol. 235, pp. 442–447, 1987). As the angiogenic diseases, the following diseases have been known; intraocular angiogenic diseases (intraocular angiogenic disease) (Ishibashi, T. "What is intraocular angiogenesis?" ed. Ishibashi, T. Intraocular Angiogenic Diseases, p. 2, Medical View Co., Tokyo, 1994) including diabetic retinopathy, occlusion of retinal vein, premature retinopathy, age-related macular degeneration, neovascular glaucoma, Eales's disease or terior lens fibroplasia, angiogenesis following cornea transplantation, glaucoma and trachoma and the like in the field of ophthalmology; psoriasis and pyogenic granuloma and the like in the field of dermatology; angioma and fibrous angioma and the like in the field of pediatrics; hypertrophic scar and proud flesh and the like in the field of surgery; rheumatic arthritis and edema sclerosis and the like in the field of internal medicine; and arteriosclerosis and myocardial infarction and the like in the field of cardiac diseases. It has additionally been known well that angiogenesis is involved in the onset and progress of tumor which generally is not called as angiogenic disease. The diseases accompanied by such abnormal angiogenic escalation have been treated in various manners, but all the diseases are refractory diseases. Therefore, a useful compound as a prophylactic or therapeutic agent therefor has been demanded.

As the substance with an activity to suppress angiogenesis, the following substances have been known; sulfated polysaccharides, platelet factor-4 (PF-4), pentosan polysulfate, TNP-470 (fumagillin derivative), irsogladine, minocycline and the like. However, their actions on the suppression of angiogenesis are not sufficient. Suppressing agents of angiogenesis are reasonable therapeutic agents of diseases accompanied by abnormality in angiogenesis. Hence, the development of a better suppressing agent of angiogenesis has been desired.

It has already been known that medroxyprogesterone acetate (abbreviated as "MPA" hereinafter) has an action to suppress angiogenesis. However, the angiogenesis suppressing action of MPA is not satisfactory. It is doubtful whether or not routine clinical dose thereof can exert the effect. At a high dose, MPA induces serious side effects due to the hormone actions as well as thrombosis. It has also been reported that FMPA (9-fluoromedroxyprogestreone acetate) has an action of inhibiting angiogenesis (Sugino et al., Chemical Pharmaceutical Bulletin, Vol. 45, No.2, pp. 421–423, 1997; Hibino et al., WO95/26974). It is found that the compound free of any hormone action is a stronger suppressing agent of angiogenesis than MPA. Nevertheless, the compound has not yet reached the stage of clinical development.

The angiogenesis suppressing action of MPA is believed not to be derived from progestin action (Yamamoto et al., International Journal of Cancer, Vol. 56, pp. 393–399, 1994; JIKIHARA et al., American Journal of Obstetrics and Gynecology, Vol. 167, No.1, pp. 207–211, 1992).

It has been reported that the FMPA described above is free of any hormone action and that progesterone does not have any activity on angiogenic suppression in a rabbit cornea assay system (Yamamoto, supra.). From structural standpoint, MPA and FMPA have a pregnane skeleton, so they are different from dienogest with an estrane skeleton.

Those capable of exerting angiogenic suppressing actions in the presence of heparin and with no activity of glucocorticoid or mineral corticoid are known as so-called angiostatic steroids (Crum et al., Science, Vol. 230, pp. 1375–1378, 1985). However, progesterone does not exert any action on angiogenic suppression although the steroid does not have any activity of glucocorticoid or mineral corticoid. On contrast, hydrocortisone as one of glucocorticoids exerts an angiogenesis suppressing action in the absence of heparin (HORI et al., British Journal of Pharmacology, Vol. 118, pp. 1584–1591, 1996). In addition to what has been described insofar, the structural specificity of such angiostatic steroids has not yet been elucidated. Accordingly, the concept thereof is not evident.

DISCLOSURE OF THE INVENTION

In such circumstances, the development of a highly effective prophylactic or therapeutic agent of diseases accompanied by abnormal angiogenic escalation has been demanded, which agent can be administered with less side effects for a prolonged term.

In intraocular angiogenic diseases, diabetic retinopathy, and particularly proliferative retinopathy rapidly cause the elimination of vision, characterized in that the diseases initially start in angiogenic symptoms on retina, and then, fibrous tissues are formed therearound and the grown fibrous tissues shrink with cicatrix, which causes retinal detachment and vitreous bleeding due to the transection of retinal vessel. Age-related macular degeneration is the disease of which the incidence is the highest in the diseases that cause choroidal angiogenesis, and the therapy by photocoagulation is only established at present. However, there is a possibility that the therapy itself impairs vision. Therefore, an ideal therapeutic method has been desired. If left to stand, malignant tumor proliferates in a host as long as the host is viable, and the proliferation makes an invasive proliferation pattern, with almost no exception. Without any treatment, the tumor then turns metastatic and finally kills the host to death. Rheumatic arthritis causes inflammation of synovial membrane at an early stage, but at its advanced stage, the disease damages cartilage and bone, while the disease deforms and dislocates joints, leading to the loss of flexibility because of the osseous rigidity. Arteriosclerosis is divided as the following three conditions; atherosclerosis, minimal arteriosclerosis and Moncheberg's type arteriosclerosis. Essentially, the disease encompasses clinically pathologic conditions with the etiology in arterial stenosis, occlusion or dilation and puncture, which are caused by arteriosclerosis. Atherosclerosis with the highest clinical incidence is observed in elastic-type arteries of broad type and muscular-type arteries of medium type, with the principal lesion lying in the intima, and the lesion then progresses into fatty stripe, fibrous erythema and complex lesions. At the most advanced stage of the complex lesion, ulcer formation, calcium deposition, bleeding and thrombus formation are observed. The present invention can overcome at least one of the symptoms described above.

The present inventors have made investigations to solve the problems. The inventors have found that dienogest unexpectedly has a strong action to suppress angiogenesis. The action is so strong that the agent might be applicable to the therapeutic treatment of diseases with abnormal angiogenic escalation as well as solid carcinoma. Additionally, the inventors have found that dienogest can exert the strong activity even if used singly, with no use of any agent in combination with the drug. Thus, the present invention has been achieved.

A first aspect of the present invention is a suppressing agent of angiogenesis, wherein the agent contains dienogest or a solvate thereof as the effective ingredient.

A second aspect of the present invention is a prophylactic and/or therapeutic agent of angiogenic diseases, wherein the agent contains dienogest or a solvate thereof as the effective ingredient.

A third aspect of the present invention is a prophylactic and/or therapeutic agent of angiogenic diseases, wherein the agent contains dienogest or a solvate thereof as the effective ingredient, particularly a prophylactic and/or therapeutic agent of intraocular angiogenic diseases, rheumatic arthritis, and arteriosclerosis.

A fourth aspect of the present invention is a prophylactic and/or therapeutic agent of sex hormone-non-dependent tumor, wherein the agent contains dienogest or a solvate thereof as the effective ingredient.

A fifth aspect of the present invention is a prophylactic and/or therapeutic agent of diseases accompanied by abnormal angiogenic escalation, wherein the agent contains dienogest or a solvate thereof as the effective ingredient, particularly a prophylactic and/or therapeutic agent of intraocular angiogenic diseases, rheumatic arthritis, and arteriosclerosis.

A six aspect of the present invention is a prophylactic and/or therapeutic agent of diseases accompanied by abnormal angiogenic escalation, wherein the agent contains dienogest or a solvate thereof as the effective ingredient, particularly a prophylactic and/or therapeutic agent of sex hormone-non-dependent tumor.

A seventh aspect of the present invention is a prophylactic and/or therapeutic agent of intraocular angiogenic diseases, rheumatic arthritis, and arteriosclerosis, wherein the agent contains dienogest or a solvate thereof as the effective ingredient.

An eighth aspect of the present invention is a suppressing agent of angiogenesis, wherein the agent contains dienogest or a solvate thereof as the effective ingredient and the agent is useful as a chemical reagent.

A ninth aspect of the present invention is the suppressing agent of angiogenesis to be used in combination with other compounds.

Each of the first to ninth aspects of the present invention mentioned above also includes a prophylactic and/or therapeutic method of each disease by a pharmaceutical composition that contains dienogest or a solvate thereof as the effective ingredient, as well as a use of dienogest or a solvate thereof in the production of an prophylactic and/or therapeutic agent of each disease.

DESCRIPTION OF THE PREFERRED EMBODIMENTS

Figure 1:
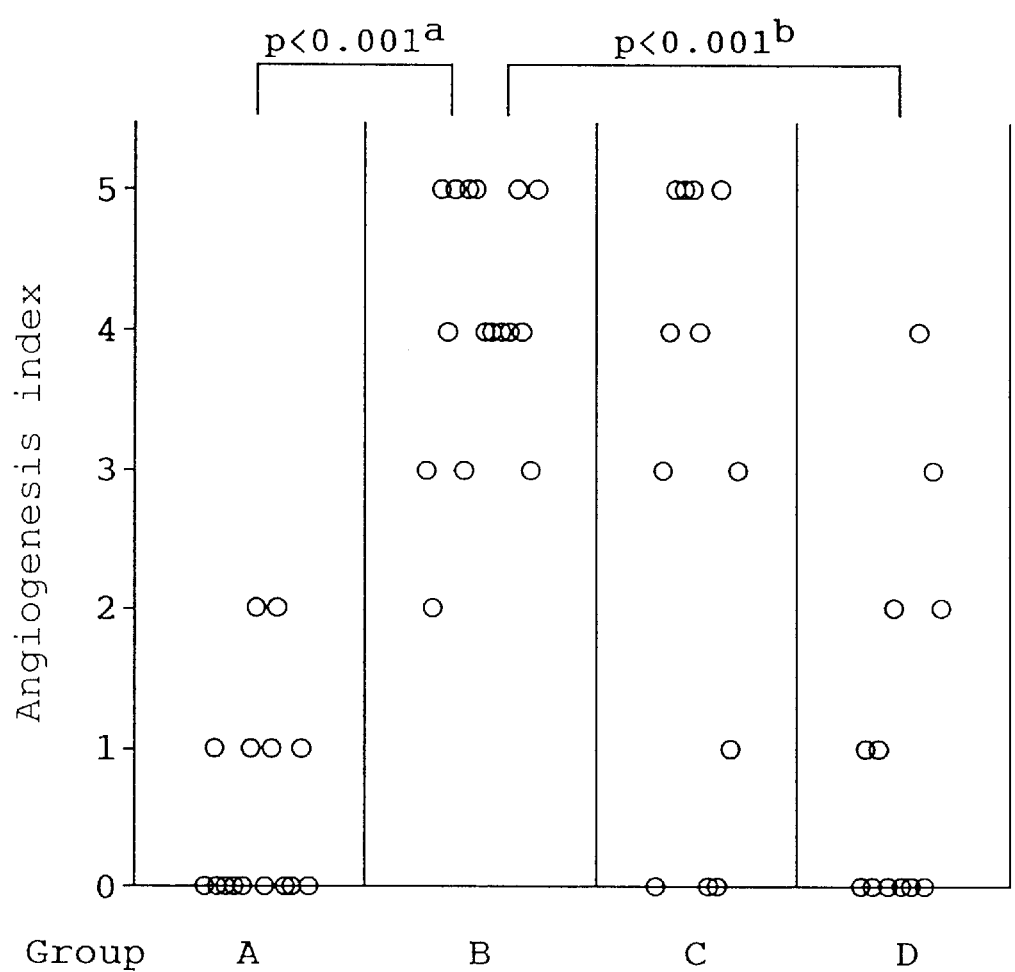
FIG. 1 is a graphs depicting the results of the Experimental Example 2 with indices.

The present invention will now be described in detail below.

The dienogest as the effective ingredient of the suppressing agent of angiogenesis of the present invention is a compound with the structure represented by the formula (I), and can form a solvate with pharmaceutically acceptable various solvents such as water, ethanol, glycerol and acetic acid.

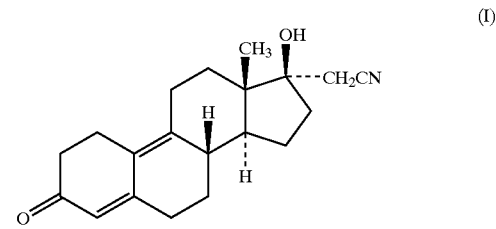

Dienogest has an angiogenesis suppressing action. Thus, the agent of the present invention is a prophylactic and/or therapeutic agent of diseases accompanied by abnormal angiogenic escalation, wherein the agent contains dienogest or a solvate thereof as the effective ingredient. The diseases with abnormal angiogenic escalation herein mean so-called angiogenic diseases and tumor, as mentioned insofar.

Specific examples of pathologic conditions of angiogenic diseases for which the agent is used as a prophylactic or therapeutic agent include intraocular angiogenic diseases, psoriasis, pyogenic granuloma, angioma, fibrous angioma, hypertrophic scar, proud flesh, rheumatic arthritis, edema sclerosis, arteriosclerosis and myocardial infarction, preferably including diabetic retinopathy, age-related macular degeneration, rheumatic arthritis, and arteriosclerosis. Alternatively, the agent can be used as a prophylactic or therapeutic agent of various types of tumor.

Diabetic retinopathy, particularly proliferation-type retinopathy, is illustrated. The disease rapidly causes the elimination of vision, characterized in that the disease initially starts in angiogenic symptoms on retina, and then, fibrous tissues are formed therearound and the grown fibrous tissues shrink with cicatrix, which causes retinal detachment and vitreous bleeding due to the transection of retinal vessel. The agent of the present invention can prevent or therapeutically treat these various symptoms; more specifically, the agent can ameliorate the symptoms or can prevent the exacerbation of the symptoms.

Age-related macular degeneration is the disease characterized by choroidal angiogenesis caused by environmental change of pigment epitheliocyte-Bruch membrane-choroid that accompanies macular change with age, and proliferative change thereof. Age-related macular degeneration causes bleeding and exudative change under retina and pigment epithelium, which are accompanied by detachment of pigment epithelium and serous retinal detachment, and is a disease in which the visual prognosis is undesirable. The agent of the present invention is effective for preventing or therapeutically treating, or more specifically ameliorating or preventing the exacerbation of these various symptoms.

Tumor is broadly grouped as benign tumor and malignant tumor. Malignant tumor is generally grouped in two types; epidermal malignant tumor and non-epidermal malignant tumor. The former is defined as cancer (or carcinoma); and the latter is defined as sarcoma. If left to stand, malignant tumor proliferates in a host as long as the host is viable, and the proliferation makes an invasive proliferation pattern, with almost no exception. Without any treatment, most of the tumor then turns metastatic. The suppressing agent of angiogenesis of the present invention can prevent the invasion of nutrient vessel or can suppress vascular metastasis, so that the tumor is degenerated or the metastasis is prevented. Thus, the agent can work as an anti-tumor agent or an agent to suppress the metastasis of tumor. On the basis of the sensitivity to sex steroids (estrogen and progesterone), malignant tumor is also divided as sex hormone-dependent tumor and sex hormone-non-dependent tumor. Sex hormone-dependent tumor means a type of tumor with sensitivity to sex hormone, among tumors generated in gynecological genital organs, such as uterine cancer, breast cancer, ovarian cancer and endometrial cancer, and prostate cancer and thyroid cancer. Sex hormone-non-dependent tumor means a type of tumor never belonging to the sex hormone-dependent tumor, specifically including cancers except genital cancer, such as stomach cancer, lung cancer, esophageal cancer, brain cancer, pancreatic cancer and cancers in the field of ophthalmology, and uterine cancer, breast cancer, ovarian cancer and endometrial cancer, these cancers having no sensitive properties to sex hormone, among cancers in the field of gynecology. Examples of sex hormone-non-dependent tumor include Kaposi's sarcoma, osteosarcoma, fibrosarcoma, lymphangiosarcoma and the like.

On contrast, benign tumor stops its growth when the tumor reaches a given size, and most of tumor does not exert invasive proliferation or does not cause metastasis. Benign tumor includes osteoma, fibroma, angioma, and myoma. Benign tumor is also divided, depending on whether or not the tumor contains any sex hormone receptor, more specifically, depending on the sex hormone sensitivity. Sex hormone-dependent tumor includes for example endometriosis, uterine leiomyoma, adenomyosis uteri, endometrial hyperplasia, and endometrial polyp; sex hormone-non-dependent tumor includes endometrial polyp and endometrial hyperplasia with no sex hormone receptor observed therein; and hyperplastic polyp observed in stomach, intestine and lung etc. The agent of the present invention is effective for a prophylactic or therapeutic treatment of these various symptoms, more specifically for ameliorating the symptoms or preventing the exacerbation of the symptoms.

The etiology of the onset of rheumatic arthritis is not evident, but attention has been drawn toward multiple-factor genetic predisposition, particularly toward the relation with HLA-D4, and viral infection. The disease causes inflammation of synovial membrane at an early stage, but at its advanced stage, the disease damages cartilage and bone, while the disease deforms and dislocates joints, leading to the loss of flexibility because of the osseous rigidity. Systemic symptoms include various symptoms such as anemia, slight fever, morning stiffness, systemic malaise, ready fatigue, body weight decrease, lymphatic nodule enlargement, and hypodermic nodule. Pathophysiologically, angiogenesis into synovial membrane is observed. The agent of the present invention can effectively prevent or treat these various symptoms. More specifically, the agent can effectively ameliorate the symptoms or prevent the exacerbation of the symptoms.

Arteriosclerosis is divided as the following three conditions; atherosclerosis, minimal arteriosclerosis and Moncheberg's type arteriosclerosis. Essentially, the disease includes clinical pathologic conditions with the etiology in arterial stenosis, occlusion or dilation and puncture, which are caused by arteriosclerosis. Atherosclerosis at the highest clinical incidence is observed in elastic arteries of broad type and muscular type arteries of medium type, with the principal lesion lying in the intima, and the lesion then progressively has fatty stripe, fibrous erythema and complex lesions. Generally, the lesion starts in twenties in abdominal aorta and progresses into chest aorta and common iliac artery, and then further progresses into coronal artery, kidney artery and mesenteric artery. At the most advanced stage of the complex lesion, ulcer formation, calcium deposition, bleeding and thrombus formation are observed. Pultaceous sclerosis of aorta forms aortic aneurysm and aortic dissecting aneurysm; pultaceous sclerosis of coronary artery mainly causes the stenosis or occlusion of the inner lumen, eventually triggering the onset of ischemic cardiac diseases. Pultaceous tumor causes stenosis at a higher level or thrombotic occlusion in cerebral artery, so that cerebral stenosis occurs clinically. Subjective symptoms of cerebral arteriosclerosis include headache, dizziness, numbness, talking disorders and the like; those of coronary arteriosclerosis include anterior chest pain and stroke, anterior chest pressure, tachypnea, and the like; those of kidney arteriosclerosis include waist pain and symptoms from hypertension, but those occur rarely; those of aorta arteriosclerosis include pain, abdominal enlargement, pulsation and the like. The agent of the present invention can effectively prevent or therapeutically treat these various symptoms; more specifically, the agent can effectively ameliorate the symptoms or prevent the exacerbation thereof. For the agent of the present invention, preferably, indications for which the efficacy of dienogest is known should be omitted. Some of the known indications of dienogest may be derived from the combination of action mechanism and angiogenesis. The present invention is not subjected to them, but the present invention is a novel therapeutic agent of diseases to which dienogest has never been indicated and for which angiogenic suppression is believed to be effective.

In addition to the use of the present agent as a therapeutic agent after the onset, the agent may be administered to an individual with enhanced activities of risk factors of individual diseases, in a prophylactic manner, prior to the onset of the diseases. For diabetic retinopathy, more specifically, the agent may satisfactorily be administered in a prophylactic manner to a patient with a diabetic history and a patient diagnosed as simple retinopathy or pre-proliferation-type retinopathy. For cancer, the agent may be administered to prevent cancer metastasis and recurrent cancer. For age-related macular degeneration, the agent may be administered in a prophylactic manner to a patient in which an inflammatory change similar to the initial pathology of arteriosclerosis such as macrophage infiltration could be confirmed. For rheumatic arthritis, the agent can be administered in a prophylactic manner to a patient who is observed to have the onset of symptoms such as morning stiffness, swelling of joints of hands and fingers, swelling of symmetric joints, and hypodermic nodules. For arteriosclerosis, the agent may be administered in a prophylactic fashion to a patient with hyperlipemia, hypertension, and diabetes mellitus, or individuals with risk factors such as smoking and drinking as daily life habits.

As a reagent, the agent may be used at tests and laboratory tests. More specifically, the agent of the present invention is useful as a method for determining whether or not a specific disease is present or a certain substance is present in body fluids, tissues or excretes, by detecting the action of the reagent on angiogenic suppression in a subjective system.

The effects of the suppressing agent of angiogenesis of the present invention are now specifically described in the following examples.

EXPERIMENTAL EXAMPLE 1

Suppressing Action of Angiogenesis According to CAM (Chick Embryo Chorioallantoic Membrane) Assay According to the method by Hayashi, et al. (Mechanism of Angiogenesis and Diseases, Medical Journal, pp. 255–266, 1996), the suppressing action of angiogenesis was tested by the CAM assay using chorioallantoic membrane of chick fertilized egg. More specifically, a hole was opened through a chick fertilized egg incubated in an incubator at 37° C. for 4 or 5 days, and then, a silicone ring of an outer diameter of 5 mm and an inner diameter of 3 mm was gently placed on the center of the chorioallantoic membrane, followed by placement of an EV (ethylene-vinyl acetate copolymer) pellet containing dienogest or MPA inside the ring. A chorioallantoic membrane on which an EV pellet with no sample was placed was used as a control group. After incubation at 37° C. for 2 days, a fat emulsion preparation was injected into each chorioallantoic membrane, so as to get a clear view of the vascular network on the chorioallantoic membrane, for subsequent observation. Formation of a non-vascular region of a diameter of 3 mm or more on the chorioallantoic membrane was defined as positive suppressing action on angiogenesis. The results are shown in Table 1.

TABLE 1

| Dose ($\mu$g/egg) | Number of chorioallantoic membranes | Number[a] of choriallantoic membrane with non-vascular region | P value [b] |
|---|---|---|---|
| 0 | 55 | 0(0) | |
| <Dienogest> | | | |
| 0.01 | 15 | 2(13.3) | <0.05 |
| 0.1 | 17 | 4(23.5) | <0.005 |
| 1 | 27 | 13(48.1) | <0.001 |
| 10 | 24 | 13(54.2) | <0.001 |
| 100 | 24 | 20(83.3) | <0.001 |
| 1000 | 24 | 22(91.7) | <0.001 |
| <MPA> | | | |
| 100 | 8 | 4(50.0) | <0.001 | a: frequency in % of the occurrence of non-vascular region, in parenthesis.
b: Data of suppressing action on angiogenesis is statistically tested by the Fisher's accurate probability test.

The results in Table 1 demonstrate that compared with the control group, dienogest at a dose of 0.01 $\mu$g/egg or more significantly increased the number of chorioallantoic membranes with non-vascular region, in a dose-dependent manner, as examined by the CAM method. In the control group, non-vascular region was not observed on the vascular network on the chorioallantoic membrane; but in the dienogest group at 1 $\mu$g/egg, non-vascular region was observed. The number of chorioallantoic membranes with non-vascular region was significantly increased at 100 $\mu$g/egg MPA treatment, compared with the number of the control group. The results indicate that dienogest has an efficacy of 10- to 100-fold that of MPA in terms of the suppressing action on angiogenesis.

EXPERIMENTAL EXAMPLE 2

Suppressing Action of Angiogenesis by Murine Dorsal Air Sac Assay

According to the method by Iwabana et al. (Cancer Invasion & Metastatic Research Manual, Kinpodo, pp. 172–176, 1995), suppressing action of angiogenesis was tested by the murine dorsal skin method. S-180 tumor cell (murine derived sarcoma) suspended in phosphate buffered saline (PBS) was injected into a Millipore chamber, and the injection opening was closed with a nylon stopper. With an injection syringe, air (10 ml) was injected into the dorsal skin of a mouse anesthetized with Nembutal, to prepare an airsak, into which the Millipore chamber was transplanted. Animals were preliminarily divided into 4 groups; a Millipore chamber injected with PBS instead of S-180 tumor cells was transplanted into animals of a non-treatment control group (group A), which were then orally given 0.5% CMC carboxymethyl cellulose sodium (0.5% CMC, Wako Pure Chemical Industries, Co.) for 5 days. For evaluation of the pharmaceutical effects, a solvent control group (group B) was orally given 0.5% CMC for 5 days; group C and group D were orally given a dienogest suspension in 0.5% CMC, at a dose of 0.1 mg/kg/day and a dose of 1 mg/kg/day, respectively, for 5 days continuously, starting from the transplantation date. The suspension was prepared by means of ultrasonication. On day following the final dosing day, the skin at the site where these chambers were transplanted was resected, to recover the chambers. After placing a black ring of the same diameter as the diameter of these chambers at the position of the chambers in place, the number of newly formed vessels of a length of 3 mm or more inside the ring was counted under a stereoscopic microscope. The number was then used as angiogenesis index and was grouped into 6 ranks from 0 to 5. Particularly because the vessels newly generated due to tumor have properties to elongate in a serpiginous manner, these vessels were discriminated from the preexisting vessels before the transplantation of the chambers. Comparison between two groups was done and analyzed by the Wilcoxon's rank sum test; while comparison between multiple groups was done and analyzed by the Dunnett's multiple comparison. The results are shown in FIG. 1.

Figure 2:
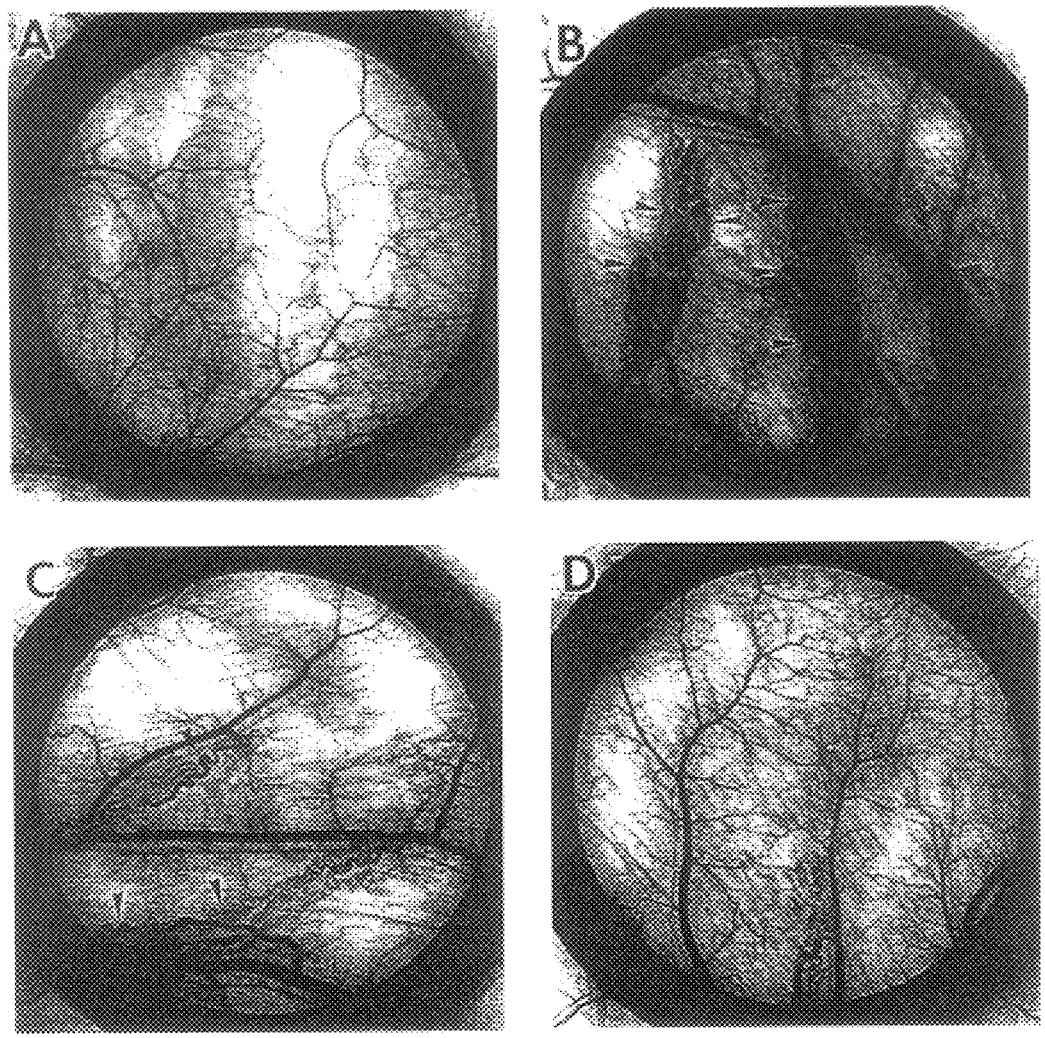
FIG. 2 is a schematic view depicting the images of the chambers under a stereoscopic microscope. A, B, C and D express the results of groups A, B, C and D, in this order.

The results in FIG. 1 show that the solvent control group (group B) transplanted with the Millipore chamber containing S-180 tumor cell significantly induced angiogenesis, compared with the non-treatment control group (group A) ($p<0.001$). Herein, "a" means comparison by the Wilcoxon's test; and "b" means comparison by the Dunnett's test. The group C administered with 0.1 mg/kg dienogest for 5 days demonstrated weak suppression of angiogenesis induced by the S-180 tumor cells; the group D administered with 1 mg/kg dienogest for 5 days significantly suppressed angiogenesis, compared with the solvent control group (group B) ($p<0.001$). Typical examples of stereoscopic microscope views of the chambers of the individual groups are shown in FIG. 2. In the groups B and C (B and C, respectively, in FIG. 2), vessels running in a serpiginous manner were observed, and such vessels are specific to angiogenesis due to tumor. In the groups A and D (A and D, respectively, in FIG. 2), however, almost no such vessel running in a serpiginous fashion could be observed.

As to the toxicity (safety) of the agent of the present invention, the effective dose of dienogest on angiogenic suppression as demonstrated in the present Experimental Example is a dose almost equal to the clinical dose (2 mg/day) of the drug which has been already used as an oral contraceptive in Germany and the safety has been verified at clinical tests of the agent (1–4 mg/day) used singly as a therapeutic agent of endometriosis. It is thus believed that no problem occurs.

The results mentioned insofar demonstrate that dienogest has a prominent action of angiogenic suppression as determined by the CMA method or in terms of cancerous angiogenesis through S-180 tumor cells. The action of dienogest on angiogenic suppression is demonstrated to be higher by 10- to 100-fold the action of the known angiogenic suppressing substance, MPA.

The dosage form of the agent of the present invention will now be described below. The suppressing agent of angiogenesis of the present invention may be satisfactory, only if the agent contains an effective amount of at least dienogest as the effective ingredient, and the agent is generally formulated together with a pharmaceutically acceptable carrier. More specifically, the agent of the present invention is a medical or veterinary composition, containing at least dienogest and a pharmaceutically acceptable carrier. The agent may satisfactorily contain appropriate additives (formulating raw materials), for example, excipients such as lactose and calcium hydrogen phosphate; binders such as powdery cellulose, dextrin, polyvinyl alcohol and polyvinylpyrrolidone; disintegrators such as carboxymethyl cellulose and carboxymethyl starch; lubricants such as sucrose fatty acid ester and magnesium stearate; colorants such as pigment; flavor such as vegetable flavor; stabilizers and the like. Specific examples of the dosage form include for example, tablets, capsules, granules, fine granules, powders, liquid solutions or suspensions, emulsions, fatty emulsions, ointments and suppositories, and additionally include sustained release formulations such as patches, tapes, and intradermal implants. The administration method includes oral administration or parenteral administrations such as intra-rectal administration, intra-vaginal administration, transdermal absorption, trans-mucosal absorption, intravenous injection, intra-cavum articulate administration, intramuscular administration or subcutaneous administration. Additionally, administration by way of injections or eye drops is also included.

The dose is about 0.5 to 10 mg/day/adult, preferably 1 to 5 mg/day/adult in one single dose to in 5 dividend doses. Depending on the age, body weight and health conditions of a patient and the dosage route, the dose and dosing number may be adjusted. Eye drops may be dropped into eyes, once to four times per day, depending on the conditions of a patient. Additionally, the use as an ophthalmic ointment can be included.

The agent of the present invention may contain other effective ingredients, other than dienogest, as the effective ingredients thereof. Such other effective ingredients are divided into compounds with an action to suppress angiogenesis and compounds with pharmacological actions except the above action.

The compound with an action to suppress angiogenesis includes agents to inhibit the binding of the receptors of basic fibroblast growth factor (bFGF) and vascular endothelial growth factor (VEGF) or to inhibit the generation of these receptors, agents to suppress the growth of vascular endothelial cells, agents to inhibit metalloprotease and the like. Preferably, the compound includes suramin compounds, dextran sulfate, β-1,3-glucan sulfate, fumagillin derivatives, minocycline, pentosan polysulfate, irsogladine, platelet factor-4 and the like.

Other compounds include agents having been used from the standpoint that the agents have an action mechanism, except angiogenic suppression, on diseases accompanied by the abnormal angiogenic escalation, preferably including anti-diabetic agents, agents for treating diabetic retinopathy, agents for treating arteriosclerosis, anti-inflammatory agents, anti-tumor agents, and anti-rheumatic arthritis agents. More specifically, anti-diabetic agents include sulfonyl urea such as glibenclamide and gliclazide; biguanides; α-glucosidase inhibiting agents such as acarbose and voglibose; agents for treating diabetic retinopathy include aldose reductase inhibiting agents such as epalrestat; agents for treating arteriosclerosis include HMG-CoA reductase inhibiting agents such as pravastatin and simvastatin, anion exchange resins such as colestyramine, fibrate based agents such as bezafibrate, antioxidants such as probucol, platelet aggregation inhibiting agents such as EPA and the like. Anti-inflammatory agents include adrenocortical steroids and non-steroidal agents such as aryl acetic acids, propionic acids and oxicam. Anti-tumor agents include alkalizing agents such as cyclophosphamide, metabolic antagonists such as amethopterin, antibiotics such as mitomycin, vegetable alkaloids and the like. Anti-rheumatic arthritis agents include oral gold formulations such as auranofin and penicillamine.

The dosage form may satisfactorily be a formulation containing dienogest and other compounds; otherwise, these may satisfactorily be administered separately. Furthermore, dienogest and the compounds may be concurrently administered to a patient; additionally, the agent may be used during the term in which conventional therapeutic agents must be reduced or terminated or must be discontinued for a while.

Examples of the present invention will be described below. The present invention is absolutely not limited to these examples.

EXAMPLE 1

| | |
|---|---|
| Dienogest | 2.0 g |
| Lactose | 87.0 g |
| Corn starch | 6.0 g |
| Magnesium stearate | 5.0 g |

The ingredients are mixed together, and each 100 mg of the resulting mixture is sealed in capsule No.3 according to Japanese Pharmacopoeia, to prepare capsules.

EXAMPLE 2

| | |
|---|---|
| Dienogest | 0.4 g |
| Lactose | 91.6 g |
| Corn starch | 50.0 g |
| Talc | 3.0 g |
| Magnesium stearate | 5.0 g |

The ingredients are appropriately mixed together, to prepare tablets by wet granule compaction process. Each tablet (150 mg) contains 0.40 mg of dienogest.

EXAMPLE 3

| | |
|---|---|
| Dienogest | 1.0 g |
| Polysorbate 80 | 1.0 g |
| Witepzol (S-55) | 98.0 g |

The ingredients are kneaded together under heating, and the resulting mixture is sealed in a plastic package, to prepare suppositories each of a weight of 1.0 g.

INDUSTRIAL APPLICABILITY

The suppressing agent of angiogenesis of the present invention has a high activity to suppress angiogenesis, and can exert therapeutic effects on angiogenic diseases such as sex hormone-non-dependent tumor and diabetic retinopathy, rheumatism, arteriosclerosis. The agent can be used as a therapeutic agent of these diseases after the onset, and furthermore, the agent can be used for an individual with enhanced risk factors of the individual diseases. Hence, the agent may possibly exert some prophylactic effect. The suppressing agent of angiogenesis of the present invention can exert its effects as a prophylactic and/or therapeutic agent of diseases accompanied by abnormal angiogenic escalation. The agent of the present invention can be used singly and additionally, the agent may be used in combination with known agents with other action mechanisms, other agents to suppress angiogenesis and other prophylactic and/or therapeutic agents of angiogenic diseases. Also, the agent of the present invention is useful as a reagent. The agent of the present invention furthermore has less side effects and can therefore be administered for a prolonged term.

What is claimed is:

1. A method of treating a patient suffering from an angiogenic disease comprising administering to a patient in need thereof an effective amount of a pharmaceutical composition that contains dienogest or a solvate thereof as the active ingredient, wherein the angiogenic disease is selected from the group consisting of intraocular angiogenic diseases, rheumatic arthritis, angioma, hypertrophic scar, proud flesh, edema sclerosis, myocardial infarction, angiogenesis following cornea transportation, glaucoma and trachoma.

2. A method of treating a patient suffering from a disease or disorder comprising administering to said patient an effective amount of a pharmaceutical composition containing dienogest or a solvate thereof as the active ingredient, wherein said disease or disorder is selected from the group consisting of stomach cancer, lung cancer, esophageal cancer, pancreatic cancer, brain cancer, cancers in the field of ophthalmology, Kaposi's sarcoma, osteosarcoma, fibrosarcoma, lymphangiosarcoma and hyperplastic polyps observed in stomach, intestine and lung.

3. The according to claim 1 or 2, wherein the composition is administered in a dosage form of about 0.5 to 10 mg/day/adult in a single to 5 divided doses.

4. The method according to claim 1 or 2, wherein the composition is administered to said patient in a dosage form of oral preparation, intra-rectal preparation, intra-vaginal preparation or transdermal absorption preparation.

5. The method according to claim 1, wherein said angiogenic disease is an intraocular angiogenic disease and the composition is administered to said patient in a dosage form of eye drops or ophthalmic ointment.

* * * * *